United States Patent [19] [11] 4,180,578
Fritschi et al. [45] Dec. 25, 1979

[54] 2,4-DIAMINO-5-(4'-METHYLTHIO)BENZYL-PYRIMIDENES, COMPOUNDS, COMPOSITIONS AND METHOD OF USE

[75] Inventors: Edgar Fritschi, Röthenbach; Walter Liebenow, Nüremberg; Jaroslav Prikryl, Erlangen-Bruck, all of Fed. Rep. of Germany

[73] Assignee: Ludwig Heumann, & Co. GmbH, Nuremberg, Fed. Rep. of Germany

[21] Appl. No.: 891,266

[22] Filed: Mar. 29, 1978

[30] Foreign Application Priority Data

May 9, 1977 [DE] Fed. Rep. of Germany ....... 2720771

[51] Int. Cl.$^2$ ................. C07D 239/48; A61K 31/505
[52] U.S. Cl. .................................... 424/251; 540/122; 424/248.56; 544/325
[58] Field of Search ........................ 544/325; 424/251

[56] References Cited

U.S. PATENT DOCUMENTS

| 3,692,787 | 9/1972 | Roth | 260/256.4 N |
| 3,822,264 | 7/1974 | Roth | 260/256.5 R |
| 3,850,927 | 11/1974 | Cresswell | 260/256.4 N |
| 3,852,276 | 12/1974 | Cresswell | 260/240 R |
| 3,855,265 | 12/1974 | Cresswell | 260/465 E |
| 4,076,810 | 2/1978 | Kompis | 424/229 |

FOREIGN PATENT DOCUMENTS

| 1720012 | 2/1967 | Fed. Rep. of Germany . |
| 1445176 | 10/1968 | Fed. Rep. of Germany . |
| 2065367 | 5/1973 | Fed. Rep. of Germany . |
| 2327786 | 5/1977 | France . |
| 957797 | 3/1964 | United Kingdom . |
| 1223881 | 3/1971 | United Kingdom . |
| 1223882 | 3/1971 | United Kingdom . |

OTHER PUBLICATIONS

Bushby, S. and G. Hitchings, "Br. J. Pharmac. Chemother.", (1968), 33, pp. 72–90.

Primary Examiner—Donald G. Daus
Assistant Examiner—Lisa Jones
Attorney, Agent, or Firm—Bernard & Brown

[57] ABSTRACT

A compound selected from a 2,4-diamino-5-thiobenzyl-pyrimidine of the formula:

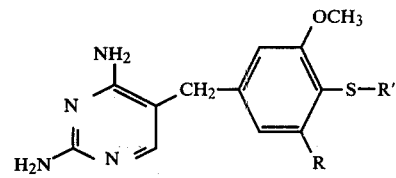

in which R is selected from hydrogen, alkyl, lower alkoxy, and halogen and R' is alkyl; and pharmacologically acceptable acid addition salts thereof. These compounds have an anti-bacterial action and are sulphonamide potentiators.

9 Claims, No Drawings

2,4-DIAMINO-5-(4'-METHYLTHIO)BENZYL-PYRIMIDENES, COMPOUNDS, COMPOSITIONS AND METHOD OF USE

This invention relates to novel pyrimidine derivatives, to processes for the preparation thereof, to pharmaceutical compositions containing them and to their use in pharmacy.

This invention provides 2,4-diamino-5-thiobenzyl pyrimidines corresponding to the following general formula I:

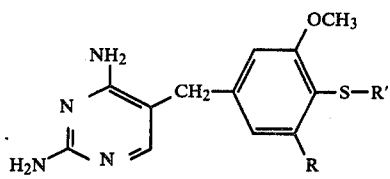

wherein R denotes hydrogen, an alkyl group, a lower alkoxy group or a halogen atom and R' denotes an alkyl group, and to their pharmacologically acceptable acid addition salts.

The invention also provides a process for the preparation of such 2,4-diamino-5-thiobenzyl pyrimidines and their salts, in which an α-benzyl-β-substituted acrylonitrile corresponding to the general formula II:

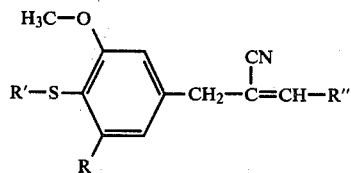

wherein R and R' have the meaning indicated above and R'' denotes an anilino, morpholino or methoxyethoxy group, is reacted with guanidine with heating, and the resulting reaction product is isolated in the usual manner and, if desired, converted into a pharmacologically acceptable acid addition salt.

The compounds according to the invention corresponding to the general formula I and their salts are new compounds. In the general formula I, R denotes hydrogen, alkyl, preferably a lower alkyl such as methyl or ethyl, lower alkoxy, or halogen, e.g. chlorine or bromine; R' denotes an alkyl group, preferably one having from 1 to 4 carbon atoms, for example a methyl or ethyl group. By "lower alkyl group" or "lower alkoxy group" is meant a group of this type having from 1 to 4 carbon atoms. As specific examples of pharmacologically acceptable acid addition salts there may be mentioned the salts of these compounds obtained with hydrochloric acid, hydrobromic acid, sulphuric acid, acetic acid, fumaric acid, maleic acid, tartaric acid, ascorbic acid, and embonic acid.

The compounds according to the invention are prepared by the reaction of an α-benzyl-β-substituted acrylonitrile corresponding to the above formula II with guanidine. The starting materials of formula II are, in turn, readily prepared by condensation of the appropriately substituted benzaldehyde with a β-substituted propionitrile corresponding to the following formula:

R''—CH$_2$—CH$_2$—CN wherein R'' has the meaning already indicated. This step is preferably carried out in a solvent. Suitable solvents are, for example, alkoxyalkanols such as the monoethyl ester of diethylene glycol the monomethyl, monoethyl or monophenyl esters of ethylene glycol and the like, dimethyl formamide and dimethyl sulphoxide.

The reaction temperature is from 20° to 90° C., preferably from 30° to 80° C. This reaction may be carried out with in the pressure range of from 0 to 5 bar but is preferably carried out at atmospheric pressure. The molar ratio of substituted propionitrile to substituted benzaldehyde is from 1:1 to 1:2, preferably 1:1.3.

The condensation reaction is advantageously carried out in the presence of basic reagents, for example an alcoholate, an anhydrous base such as sodium methylate or ethylate, potassium tertiary butylate, sodium hydroxide or potassium hydroxide or an organic base such as benzyltrimethyl ammonium hydroxide.

After completion of the reaction, the solvent remaining is distilled off and the condensation product is isolated in known manner, for example by dissolving of the residue left from distillation of the solvent in a solvent such as dichloroethane, washing of the organic phase with water until neutral, drying with a dehydrating agent such as calcium chloride, evaporation of the solvent and distillation of the resulting residue or crystallization from a suitable solvent.

The resulting α-benzyl-β-substituted acrylonitrile compound corresponding to formula II is then reacted with guanidine to form the corresponding, new 2,4-diamino-5-thiobenzyl pyrimidine. This reaction is also carried out in a solvent, for example an alcohol such as methanol or ethanol, or in a solvent of the type which has been described above in connection with the preparation of the acrylonitrile compound.

The reaction temperature for the condensation with guanidine is from 65° to 145° C., preferably from 70° to 100° C. The reaction may be carried out within a pressure range of from 0 to 5 bar. It is preferably carried out at atmospheric pressure.

The molar ratio of α-benzyl-β-substituted acrylonitrile compound to guanidine is from 1:1 to 1:5, preferably from 1:2 to 1:3.

The guanidine used in this stage has preferably been prepared from guanidine hydrochloride by reaction with a base, e.g. with a sodium methylate solution.

After completion of the reaction, the solvent is distilled off and the desired product is isolated from the cooled reaction mixture by the usual methods, e.g. concentration of the solution by evaporation under vacuum. The crude product may be purified in the usual manner, for example by reprecipitation or recrystallization.

The compounds according to the invention have a powerful anti-bacterial action comparable to that of the known compound, 2,4-diamino-5-(3'4',5'-trimethoxybenzyl)-pyrimidine, i.e. trimethoprim (TMP) (Table I).

Table I

| | MIC values in μg/ml (serial dilution test, DST-Agar) | | |
|---|---|---|---|
| | | Geometrical mean value of MIC in μg/ml | |
| Bacteria | n | 2,4-diamino-5-(3',5'-dimethoxy-4'-S-methyl-benzylpyrimidine | TMP |
| E. Coli | 15 | 0.142 | 0.108 |
| Proteus | 3 | 0.992 | 0.625 |

Table I-continued

| | | MIC values in μg/ml (serial dilution test, DST-Agar) | |
|---|---|---|---|
| | | Geometrical mean value of MIC in μg/ml | |
| Bacteria | n | 2,4-diamino-5-(3',5'-dimethoxy-4'-S-methyl-benzylpyrimidine | TMP |
| Klebsiellae | 3 | 0.248 | 0.496 |
| Enterococcus | 2 | 0.156 | 0.078 |

The toxicity, however, is considerably lower than that of trimethoprim (Table II) so that the compounds according to the invention have a better therapeutic index, i.e. a wider therapeutic range.

Table II

LD$_{50}$ values of TMP and 2,4-diamino-5-(3',5'-dimethoxy-4'-S-methyl)-benzylpyrimidine (mouse, intragastral administration) (determined according to J.T. Litchfield and F. Wilcoxon in "J. Pharmacol. Exper. Therap. 96,99 (1949)")

| Substance | LD$_{50}$ mg/kg | safety limit in mg/kg $p = 0.05$ lower | upper |
|---|---|---|---|
| 2,4-diamino-5-(3',5'-dimethoxy-4'-S-methyl)-benzylpyrimidine | >5000.0 | — | — |
| TMP | 2764.5 | 2105.5 | 3629.8 |

It was surprisingly also found that compounds of the thiobenzylpyrimidine series are much more effective sulphonamide potentiators than trimethoprim, as is evidenced from the low FIC indices (Table III). The FIC index is the sum of the quotients of minimum inhibitory concentration values (MHK values) of each component of the combination in the mixture and alone, and is a numerical expression of the sulphonamide potentiating effect.

The lower the FIC index, the more powerful is the potentiating action of the compound.

Table III

FIC indices for E. Coli
(determined according to J. Biol. Chem, 208, 477–88(1954)

| Proportions in mixture | TMP + SMZ FIC | | 2,4-diamino-5-(3',5'-dimethoxy-4'-S-methyl)-benzylpyrimidine + SD | |
|---|---|---|---|---|
| | n | | n | |
| 1 : 2 | 14 | 0.732 | 11 | 0.502 |
| 1 : 4 | 22 | 0.630 | 11 | 0.438 |
| 1 : 8 | 22 | 0.614 | 11 | 0.359 |
| 1 : 16 | 22 | 0.625 | 11 | 0.257 |
| 1 : 32 | 5 | 0.800 | 11 | 0.298 |

SMZ : sulphamethoxazole
SD : sulphadiazine

Table IV shows that the more powerful potentiating action of these substances is not achieved by greater bioavailability.

TABLE IV

| Serum level, rat (50 mg/kg i.g.) | | |
|---|---|---|
| Compound | μg/ml Time in h 0.5 | 1 |
| 2,4-diamino-5-(3',5'-dimethoxy-4'-S-methyl)-benzylpyrimidine | 5.0 | 2.7 |
| TMP | 4.5 | 3.3 |

The compounds according to the invention can therefore be used to advantage in combination preparations containing sulphonamides, e.g. sulphadiazine, sulphadiimidine, sulphamethoxazole and the like, because a considerable improvement in the anti-bacterial activity is thereby achieved.

The present invention therefore also relates to a pharmaceutical composition, e.g. an anti-bacterial agent, which is characterised in that it contains at least one of the compounds of the general formula I in addition to the usual auxiliary agents and excipients.

Combinations of the following excipients may be used as auxiliary agents for dry forms of application: cellulose, dextrose, corn starch, saccharose, talcum, magnesium stearate, calcium hydrogen phosphate, lactose, gelatine, polyvinylpyrrolidine. As auxiliary agents for liquid forms of application there may be used, for example, solutions or suspensions of carboxymethyl cellulose, cellulose, sorbitol, saccharose, sweeteners and colourants and flavouring substances in water. Compounds of formula I in the form of buffer solutions are suitable for parenteral administration.

The invention will now be illustrated with the aid of examples.

EXAMPLE 1

Preparation of
2,4-diamino-5-(3',5-dimethoxy-4'-methylthio)-benzyl-pyrimidine (a) preparation of
α-(3,5-dimethoxy-4-methylthio)-benzyl-β-anilino-acrylonitrile 119.5 g (0.56 mol) of 3,5-dimethoxy-4-methylthio-benzaldehyde, 92.8 g (0.63 mol) of anilinopropionitrile, 110 ml of dimethylsulphoxide and 273 ml of tertiary butanol are introduced into a 1 liter 3-necked flask and heated to 30°–40° C. on a water bath (until a clear solution is obtained). The resulting solution is then cooled to 10° C. in an ice bath and 47.5 g (0.42 mol) of potassium tertiary butylate are added at such a rate that the reaction temperature does not rise above 25° C. Heating is continued for 5 hours at 50° C. after all the potassium tertiary butylate has been added, and the solvent is then distilled off under vacuum. The residue is taken up with 760 ml of methylene chloride and washed twice, each time with 450 ml of water, and the methylene chloride phase is concentrated by evaporation under vacuum. The residue is then worked up without purification.

Yield: 170 g.

(b) Reaction of
α-(3,5-dimethoxy-4-methylthio)-benzyl-β-anilinoacrylonitrile with guanidine 1,120 ml of ethanol are added to 170.0 g (0.5 mol) of α-(3,5-dimethoxy-4-methylthio)-benzyl-β-anilino-acrylonitrile and 156.0 g (1.63 mol) of guanidine hydrochloride in a 2 liter 3-necked flask and the mixture is heated to 80° C. with stirring. 265.5 ml of 30% (1.46 mol) of sodium methylate are then added dropwise over a period of 1 hour and ca. 600 ml of solvent are distilled off at the same time. The reaction mixture is then heated under reflux for 5 hours, sodium chloride is removed by suction filtration after cooling, and the ethanolic solution is concentrated by evaporation under vacuum. The precipitated crude product is dissolved in 500 ml of water with the addition of acetic acid and active charcoal in the heat, the hot solution is filtered and the base is precipitated by the addition of ammonia.

Melting Point: 229°–230° C.

$C_{14}H_{18}N_4O_2S$—Calculated: C 54.89%, H 5.92%, N 18.28%, O 10.45%, S 10.46%; Found: C 55.11%, H 5.78%, N 17.88%, O 11.05%, S 9.95%.

EXAMPLE 2

Preparation of 2,4-diamino-5-(3'-methoxy-4'-methylthio)-benzyl-pyrimidine (a) Preparation of α-(3-methoxy-4-methylthio)-benzyl-β-anilino-acrylonitrile 4.6 g (25.2 mmol) of 3-methoxy-4-thiomethyl-benzaldehyde, 4.18 g (27 mmol) of anilinopropionitrile, 5.4 g of dimethyl sulphoxide and 12.3 ml of tertiary butanol are heated to 40° C. until a clear solution is obtained. This solution is then cooled to 10° C. and 2.1 g (19.6 mmol) of potassium tertiary butylate are added at such a rate that the reaction temperature does not rise above 25° C. The mixture is then heated to 50° C. for 5 hours, the solvent is distilled off and the residue is taken up with 80 ml of methylene chloride. After the usual treatment with water, the organic phase is concentrated by evaporation under vacuum.

Yield: 8.0 g.

This product may be worked up without purification.

(b) Reaction of α-(3-methoxy-4-methylthio)-benzyl-β-anilinoacrylonitrile with guanidine 8.0 g (0.026 mol) of α-(3-methoxy-4-methylthio)-benzyl-β-anilino acrylonitrile and 5.4 g (0.062 mol) of guanidine hydrochloride are heated to 80° C. in 60 ml of ethanol, and thereafter 9.1 ml (0.05 mol) of sodium methylate are added drop-wise. After addition of sodium methylate, heating is continued for 4 hours under reflux, the ethanol is then distilled off, the residue is taken up with a small quantity of methanol and the desired product is left to crystallize in the cold.

After re-crystallization from 50% ethanol, the compound melts at 193°–194° C.

$C_{13}H_{16}N_4OS$ (276.4)—Calculated: C 56.59%, H 5.83%, N 20.29%, O 5.79%, S 11.66%; Found: C 56.66%, H 5.99%, N 19.87%, O 6.10%, S 11.29%.

EXAMPLE 3

Preparation of 2,4-diamino-5-(3'bromo-4'-methylthio-5'-methoxy)-benzylpyrimidine This compound is prepared by a method analogous to that of Example 1. After re-crystallization from ethanol, the compound melts at 230°–233° C.

$C_{13}H_{15}BrN_4OS$ (355.3)—Calculated: C 43.95%, H 4.26%, Br 22.49%, N 15.77%, O 4.50%, S 9.02%; Found: C 44.40%, H 4.28%, Br 22.24%, N 15.42%, O 4.67%, S 8.92%.

EXAMPLE 4

Preparation of 2,4-diamino-5-(3'5'-dimethoxy-4'-thiobutyl)-benzyl-pyrimidine (a) Preparation of α-(3,5-dimethoxy-4-thiobutyl-benzyl)-β-morpholino-acrylonitrile 4.5 g of sodium are carefully added to 165 ml of methoxy ethanol. When the sodium has dissolved, 26.4 g (0.189 mol) of morpholinopropionitrile are added and the whole solution is heated to 100° C. 42.0 g (0.165 mol) of 3,5-dimethoxy-4-thiobutyl-benzaldehyde dissolved in 90 ml of methoxy ethanol are then added dropwise, heating is continued at this temperature for 1 hour, and the solution is evaporated under vacuum. The residue is taken up with methylene chloride and washed with water, and the solvent is distilled off. The yellow oil obtained as residue may be worked up without purification.

Yield: 62.0 g (b) Preparation of α-(3,5-dimethoxy-4-thiobutylbenzyl)-β-(4'-chloroanilino)-acrylonitrile 62.3 g (0.165 mol) of α-(3,5-dimethoxy-4-thiobutyl)-β-morpholino-acrylonitrile and 21.0 g (0.165 mol) of p-chloroaniline are added to 170 ml of isopropanol and the mixture is heated to 80° C. 140 ml of concentrated hydrochloric acid are then added dropwise and the mixture is heated under reflux for 1 hour. The desired product crystallizes after the addition of 80 ml of water and cooling of the reaction solution. After washing of the precipitate, the compound melts at 117°–119° C.

Yield: 38.0 g.

(c) Reaction of α-(3,5-dimethoxy-4-thiobutylbenzyl)-β-(4'-chloroanilino)-acrylonitrile with guanidine 38.0 g (0.091 mol) of the compound prepared by method (b) and 38.1 g (0.099 mol) of guanidine hydrochloride are heated to 80° C. in 200 ml of methoxyethanol, and 64.3 ml (0.353 mol) of sodium methylate (5.5 molar) are then added dropwise. The reaction mixture is then heated under reflux for 2 hours, suction filtered to remove the precipitated sodium chloride, and evaporated under vacuum. 50 ml of methanol are added to the residue and the product which precipitates is suction filtered.

Crude Yield 24.0 g.

To purify the crude product, it is dissolved in 1,000 ml of water with the addition of 5 ml of glacial acetic acid and heated to boiling, and 1.0 g of active charcoal is added. After filtration over celite, 7 ml of 25% ammonia are added to the hot solution and the desired product is left to crystallize on cooling.

Yield: 19.5 g.

Melting point 188.7°–189.2° C.

$C_{17}H_{24}N_4O_2S$ (348.47)—Calculated: C 58.60%, H 6.94%, N 16.08%, S 9.20%; Found: C 58.41%, H 6.90%, N 15.81%, S 8.97%.

EXAMPLE 5

Preparation of 2,4-diamino-5-(3'-chloro-4'-methylthio-5-methoxy)-benzylpyrimidine The compound is prepared by a method analogous to that of Example 4. After purification, the compound melts at 236.9°–237.6° C.

$C_{13}H_{15}ClN_4OS$ (318.8)—Calculated: C 50.24%, H 4.86%, Cl 11.41%, N 18.03%; Found: C 50.32%, H 5.10%, Cl 11.21%, N 18.16%.

We claim:

1. A compound selected from a 2,4-diamino-5-thiobenzylpyrimidine of the formula:

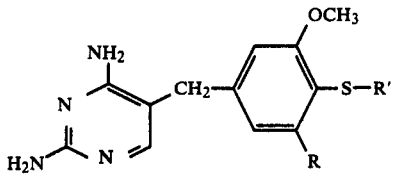

in which R is selected from hydrogen, lower alkyl, lower alkoxy, and halogen, and R' is lower alkyl; and pharmacologically acceptable acid addition salts thereof.

2. A compound as claimed in claim 1 which is 2,4-diamino-5-(3',5'-dimethoxy-4'-methylthio)-benzylpyrimidine.

3. A compound as claimed in claim 1 which is 2,4-diamino-5-(3'-methoxy-4'-methylthio)-benzylpyrimidine.

4. A compound as claimed in claim 1 which is 2,4-diamino-5-(3'-bromo-4'-methylthio-5'-methoxy)-benzylpyrimidine.

5. A compound as claimed in claim 1 which is 2,4-diamino-5-(3'5'-dimethoxy-4'-thiobutyl)-benzylpyrimidine.

6. A compound as claimed in claim 1 which is 2,4-diamino-5-(3'-chloro-4'-methylthio-5'-methoxy)-benzylpyrimidine.

7. A pharmaceutical composition suitable for treating a bacterial infection, said composition consisting essentially of a compound as claimed in claim 1 and a pharmaceutically acceptable carrier or diluent.

8. A method for treating a bacterial infection in a patient which comprises administering an effective amount of a compound as claimed in claim 1.

9. A method for treating a bacterial infection in a patient which comprises administering an effective amount of a compound as claimed in claim 1 in combination with a sulphonamide.

* * * * *